United States Patent [19]

Petereit et al.

[11] Patent Number: 5,292,522
[45] Date of Patent: Mar. 8, 1994

[54] AQUEOUS FILM COATING AGENT FOR SOLID MEDICAMENTS

[75] Inventors: Hans-Ulrich Petereit, Darmstadt; Manfred Assmus, Bickenbach; Klaus Lehmann, Rossdorf, all of Fed. Rep. of Germany

[73] Assignee: Röhm GmbH, Darmstadt, Fed. Rep. of Germany

[21] Appl. No.: 998,882

[22] Filed: Dec. 28, 1992

Related U.S. Application Data

[63] Continuation of Ser. No. 825,006, Jan. 27, 1992, abandoned, which is a continuation-in-part of Ser. No. 707,320, May 28, 1991, abandoned, which is a continuation of Ser. No. 541,278, Jun. 20, 1990, abandoned.

[30] Foreign Application Priority Data

Jun. 20, 1989 [DE] Fed. Rep. of Germany ....... 3920082

[51] Int. Cl.$^5$ .................................................. A61K 9/16
[52] U.S. Cl. ...................................... 424/490; 424/480
[58] Field of Search ................ 424/490, 480; 524/523, 524/548

[56] References Cited

U.S. PATENT DOCUMENTS

| | | | |
|---|---|---|---|
| 4,330,338 | 5/1982 | Banker | 424/480 |
| 4,452,862 | 6/1984 | Markert | 524/548 |
| 4,644,031 | 2/1987 | Lehmann | 524/523 |
| 5,008,113 | 4/1991 | Kokubo | 424/490 |

*Primary Examiner*—Thurman K. Page
*Assistant Examiner*—William E. Benston, Jr.

[57] ABSTRACT

A water insoluble lipophilic emulsifier having a hydrophile-lipophile balance (HLB) of 3.5 to 7, added to an aqueous dispersion containing a polymer comprising acrylic acid, methacrylic acid, their alkyl esters, and/or their alkylaminoalkyl esters, acts as a lubricant and parting agent when the resulting mixture is used for coating pharmaceutical dosage forms and prevents the pharmaceutical dosage forms being coated from sticking to one another and to the walls of the coating apparatus used.

9 Claims, No Drawings

AQUEOUS FILM COATING AGENT FOR SOLID MEDICAMENTS

This application is a continuation of 07/825,006 filed Jan. 1, 1992,which is a continuation in part of Ser. No. 07/707,320 filed May 28, 1991, which is a continuation of Ser. No. 07/541,278 filed Jun. 20, 1992, all now abandoned.

The present invention relates to a film forming aqueous coating composition for pharmaceutical products which contains as vehicle a dispersed film forming polymer comprising acrylic acid, methacrylic acid, their alkyl esters, and/or their aminoalkyl esters, to methods for making the same, and to methods for coating pharmaceutical products with such a composition.

To be suitable for the coating of pharmaceutical products, the coating composition must be produced from components which in the light of present day knowledge are pharmacologically safe and whenever possible meet pharmacopoeial standards.

Film forming aqueous coating compositions intended for pharmaceutical products and containing dispersed polymers comprising acrylic acid and/or methacrylic acid or their aminoalkyl esters and/or their alkyl esters as a binder have proved themselves for years in the manufacture of pharmaceutical products. Aqueous dispersions offer the advantage over the organic polymer solutions priorly employed that only water vapor, which can readily be discharged to the atmosphere, will escape during their use, whereas the vapors of organic polymer solutions have to be recovered or destroyed by expensive methods.

The surfaces of pharmaceutical products which are coated with film forming coating dispersions pass during drying through a phase in which the coating film is still mechanically unstable and tacky and the coated pharmaceutical dosage units tend to stick to one another. The whole batch may then agglomerate, or portions of the coating film may be torn off through contact with other units. Such flaws will result in undesired release characteristics of the active ingredient of the coated pharmaceutical product.

To cope with this tacky phase without adversely affecting the properties of the product, it is general practice to add lubricating agents or parting (separating) agents to the coating dispersion. (The term "release agent" is intentionally avoided here to prevent confusion with the release properties of a coated dosage form, i.e. the nature of the liberation of active ingredient from the coated dosage form after ingestion.)

A lubricating effect is sufficient if dosage unit forms, moistened with the liquid coating agent, do not adhere to one another during the coating process and through their mutual motion effect a uniform distribution of the coating agent on the surface of the dosage unit forms. However, the lubrication must not be so great that the charge of dosage unit forms moves as a whole in the coating kettle without mutual motion of the individual dosage unit forms relative to one another.

A parting or separating effect is sufficient if, when drying coated dosage unit forms, they do not adhere to one another or to the wall of the coating kettle, even for short periods of time. On the other hand, they also should not promote the formation of free-roaming coating agent.

The conventional lubricating and parting agents are finely divided solids, and particularly silicates such as talc or finely divided silicic acid. Although the latter are regarded as pharmacologically safe, they are increasingly being avoided by many drug manufacturers because of supposed risks. These separating agents cannot be permanently dispersed in the aqueous coating compositions. Coating dispersions therefore must be prepared just before they are used and have to be constantly stirred during spraying.

The coating of pharmaceutical dosage forms without such agglutination inhibiting additives calls for great skill and a very slow operating procedure. Published German patent application 23 40 060 describes a process which uses the fluidized bed technique to first coat soft-gelatin capsules with an organic coating solution and then with an aqueous coating dispersion. The latter does not contain any powdered additives to inhibit agglutination and therefore has to be sprayed on very carefully. The relatively low bulk density of the capsules facilitates coating; capsules show less tendency to agglutinate in a fluidized bed than do compact dosage forms.

The coating dispersions used according to published German patent application 23 40 060 may contain plasticizing additives such as glycols, polyglycols, glycerine, triacetin, or ethoxylated partial glycerides of fatty acids of medium chain length. Glycerine monooleate is also mentioned as a suitable plasticizer. Depending on the manufacturing method, this product, structured like a surfactant, has a hydrophile-lipophile balance of from 2.6 to 4, is insoluble in water, and is not self-emulsifying.

The invention has as its object to provide a film forming aqueous coating composition for pharmaceutical products which is composed of pharmacologically safe components, can be stored in ready to use form with or without incorporated pigments or fillers, and can be applied to solid pharmaceutical dosage forms without the use of parting agents such as talc, silicic acid, or other agglutination inhibiting additives, and without the dosage unit forms sticking together.

The novel coating compositions of the invention contain:

(a) A film forming dispersed polymer comprising at least one member selected from the group consisting of acrylic acid, methacrylic acid, their alkyl esters, and their alkylaminoalkyl esters, and (b) a water insoluble organic lipophilic emulsifier having a hydrophile-lipophile balance (HLB) from 3.5 to 7.

Such lipophilic emulsifiers have the unexpected effect of preventing agglutination of the pharmaceutical dosage forms during the coating process. Moreover, they counteract any tendency of the finished dosage forms to agglutinate under unfavorable storage conditions. This effect can be enhanced by applying a thin film of the lipophilic emulsifier to the dosage forms from an aqueous dispersion which contains no other coating composition at the end of the coating process It is hypothesized that, on drying, the lipophilic emulsifiers separate from the coating composition and form a non-adherent boundary layer having reduced adhesion at the surface of the coating. Thus there is no need to add solids not present in a stable dispersion, especially talc. On the other hand, the lipophilic emulsifiers have a dispersing effect on commonly used pigments and fillers, which therefore can be used without adversely affecting storage stability.

Lipophilic emulsifiers are capable of forming stable dispersions in aqueous dispersions of the aforesaid polymers over the claimed hydrophile-lipophile balance (HLB) range. This is not true of lipophilic emulsifiers having a lower HLB value, which during storage will separate from the coating composition. When the HLB value is greater than 7, the emulsifier is water soluble and there is no agglutination inhibiting effect. The preferred HLB range extends from 3.5 to 5.

The hydrophile-lipophile balance is a measure, introduced by Griffin in 1950, of the hydrophilicity and lipophilicity, respectively, of nonionic surfactants. It can be determined experimentally by the phenol titration method after Marszall. [See Parfümerie Kosmetik, vol. 60, 1979, pp. 444–448; for additional bibliography, refer to Römpps Chemie-Lexikon, 8th ed., vol. 3 (1983), p. 1715.]

Typical examples of the lipophilic emulsifiers to be used in accordance with the invention are listed below along with their trade names.

| Chemical designation | HLB | Trade name |
| --- | --- | --- |
| Ethylene glycol monolaurate | 3.6 | "Cithrol EGML" |
| Diethylene glycol monooleate | 5.0–5.7 | "Cithrol DGMO" |
| Diethylene glycol monostearate | 4.4–5.0 | "Cithrol DGMS" |
| Diethylene glycol distearate | 5.5 | "Cithrol DGDS" |
| Propylene glycol monolaurate | 3.6 | "Cithrol PGML" |
| Propylene glycol monooleate | 3.9 | "Cithrol PGMO" |
| Propylene glycol ricinoleate | 3.6 | "Cithrol PGMR" |
| Propylene glycol monostearate | 3.2 | "Cithrol PGMS" |
| Dipropylene glycol monooleate | 5.3–6.0 | "Cithrol DPGMO" |
| Glycerol monostearate | 3.5–3.8 | "Abracol, Cutina GMS" |
| Glycerol distearate | 3.4–4.2 | "Cithrol GDS" |
| Glycerol monolaurate | 4.9–5.6 | "Cithrol GML" |
| Glycerol monoricinoleate | 3.6 | "Cithrol GMR" |
| Sorbitan sesquioleate | 3.7 | "Arlacel C" |
| Sorbitan monooleate | 4.3 | "Atlas G-4884", "Span 80", "Atpet" |
| Sorbitan monostearate | 4.7 | "Span 60" |
| Sorbitan monoisostearate | 4.7 | "Crill 6" |
| Polyethylene glycol-200-dilaurate | 6.0 | "Cithrol 2DL" |
| Polyethylene glycol-300-diricinoleate | 5.0 | "Cithrol 3DR" |
| Polyoxyethylene (2) cetyl alcohol | 5.3 | "Brij 52" |
| Polyoxyethylene (2) stearyl alcohol | 4.9 | "Brij 72" |
| Polyoxyethylene (2) oleyl alcohol | 4.9 | "Brij 92" |
| Polyoxyethylene cetyl/oleyl alcohol | 6.0 | "Atlas G-70140" |
| Polyoxyethylene (6) sorbitan beeswax derivative | 5.0 | "Atlas G-1702" |
| Polyoxyethylene (20) sorbitan beeswax derivative | 5.0 | "Atlas G-1726" |

The chemical composition of the products on the market often does not correspond exactly to the chemical name indicated. Apart from the fact that polyhydric alcohols are mostly mixtures of isomers, they are usually mixed with varying proportions of higher or lower esterified alcohols. For example, the products marketed as monoglycerides of fatty acids contain amounts of free glycerine and of di- and tri-glycerides as well as of free fatty acids which may represent as much as 50 percent of the product and have a corresponding influence on the HLB. Products sold as glycerine monooleate, for example, may have HLB values ranging from 2.7 to 4. Whether a particular lipophilic emulsifier is suitable for the purposes of the invention therefore depends not so much on its chemical name as on the measured HLB value.

The lipophilic emulsifier preferably is from 0.1 to 10 percent by weight of the polymer, suitably from 0.1 to 8 percent by weight for certain emulsifiers such as sorbitan monooleate. When the coating composition contains pigments or fillers, a lipophilic-emulsifier content between 2 and 10 weight percent will be advantageous, again with 8 weight percent being a preferred upper limit for certain emulsifiers. Amounts exceeding 10 or 8 weight percent may impair the adhesion of the polymer film and lead to nonuniform coatings.

Dispersions of polymers based on acrylic and/or methacrylic acid and/or their alkyl esters which are film forming from an aqueous dispersion have proved themselves as coating compositions for solid pharmaceutical dosage forms. Dispersions of water insoluble emulsion polymers are known from German patents 16 17 351 (=GB 1,213,248) and 18 14 669 (=GB 1,272,139), films of which polymers are made permeable to active substances by means of additives. Without such additives, films from emulsion polymers according to German patent 21 35 073 (=GB 1,393,374), which contain functional units having carboxyl groups, in addition to units of acrylic and/or methacrylic esters, are soluble in intestinal juice. If the carboxyl groups are replaced by amino groups, coatings soluble in gastric juice are obtained. According to published German patent application 34 05 378 (=U.S. Pat. No. 4,644,031) or 35 24 337, coatings for pharmaceutical products having precisely defined release characteristics for the enclosed active substance can be produced by mixing film forming dispersions containing water insoluble emulsion polymers with film forming dispersions of alkali soluble emulsion polymers containing carboxyl groups or of acid soluble emulsion polymers containing amino groups. German patent 3,106,449 (=U.S. Pat. No. 4,452,862) also discloses useful coating dispersions for pharmaceutical products which contain acid soluble polymers comprising alkyl esters and specific aminoalkyl esters of acrylic and/or methacrylic acid. Polymers which contain quaternary ammonium groups and are soluble or capable of swelling regardless of pH value, and which can be used in dispersed form to coat pharmaceutical products, are known from European patent 181,515 (=U.S. Pat. No. 4,737,357).

The coating dispersions are usually produced directly by emulsion polymerization of the appropriate acrylic and/or methacrylic monomers. However, stable coating dispersions can also be produced from powdered polymers if these are given self-emulsifying properties by means of salt-like groups. According to published German patent application 32 08 791 (=U.S. Pat. No. 4,520,172), for example, spray dried emulsion polymer powders containing carboxyl groups are dispersed by the addition of alkali to give stable aqueous coating materials. According to European patent 181,515, polymers containing quaternary ammonium groups can be dispersed in water to form stable dispersions.

The dispersed polymer can be regarded as film forming if it dries to form a continuous film under the conditions under which solid pharmaceutical dosage forms are coated by conventional coating methods. The drying temperature usually ranges from 10° C. to 80° C., and the minimum film forming temperature, determined in conformity with DIN 53787, should therefore be within that range and should preferably not exceed 30° C. The amount of polymer in the coating composition generally ranges from 5 to 50 weight percent, and preferably from 10 to 20 weight percent.

For the purposes of the invention, typical polymers are homopolymers or copolymers of acrylic monomers. They may be neutral and composed entirely or almost entirely of alkyl esters of acrylic acid and/or methacrylic acid. Polymers which are soluble or capable of swelling in the acidic or weakly alkaline fluids of the gastrointestinal tract contain monomer units with polar groups, mostly as comonomer units, in addition to nonpolar units such as the alkyl esters of acrylic acid and/or methacrylic acid. The polymers used in accordance with the invention therefore are preferably composed of 30 to 70 weight percent of acrylic acid and/or methacrylic acid, or of from 5 to 50 weight percent of their alkylaminoalkyl esters, alkyl esters of acrylic acid and/or methacrylic acid making up the balance or even the entire composition. Optionally, up to 50 weight percent of other, ethylenically unsaturated monomers free radically copolymerizable therewith may go into the composition of the polymers. Of the alkyl esters, those having from 1 to 4 carbon atoms in the alkyl group are preferred. In the alkylaminoalkyl esters, the alkyl group bearing the amino group or groups may have from 1 to 5 carbon atoms while the alkyl substituents on the amino group may have from 1 to 4 carbon atoms. From the pharmacological point of view, ethyl acrylate and methyl methacrylate are the ester components best suited.

The composition of the polymer should be chosen so that the film formed from it is dry and hard, that is not tacky, but not brittle either. This profile of properties is achieved when the dynamic glass transition temperature of the polymer film (also referred to as $T_{max}$ or $T_{g[dyn]}$) in conformity with DIN 53445 ranges from $-10°$ C. to $100°$ C. and preferably from $10°$ C. to $60°$ C.

The dynamic glass transition temperature can be adjusted to the desired level through the composition of the polymer or, if mixtures of several polymers are used, through the composition and the proportions of the individual polymers. As is known, acrylic esters and higher methacrylic esters when used as comonomers will lower the dynamic glass transition temperature while acrylic acid or methacrylic acid and lower methacrylic esters will raise it. The proportion of acrylic acid and/or methacrylic acid depends, as is known, on the required solubility characteristics or the diffusion permeability of the coating film. The remaining proportion of monomers is then selected from the hardening and softening monomers in such a way that the desired glass transition temperature is obtained.

If desired, the hardness of the film can also be reduced or its elasticity and flexibility increased by means of plasticizers. Suitable plasticizers are polyethylene glycols, triacetin, and esters of citric acid, for example.

The polymer is usually stabilized with anionic and/or nonionic water soluble emulsifiers with HLB values ranging from 10 to 20. They may represent up to 10 weight percent of the coating composition. Commonly used water soluble emulsifiers are sodium lauryl sulfate and polysorbate, for example.

The aqueous coating composition may be composed solely of the polymer dispersed in the water phase and of the lipophilic emulsifier and will then give clear films, the solubility and permeability of which depend on the composition of the polymer. The can be soluble or insoluble in the gastric fluid, and essentially diffusion-permeable, but with increasing pH value become soluble or capable of swelling in intestinal juice. The release characteristics for the enclosed active substance are not appreciably altered by the content of lipophilic emulsifier.

It is frequently desired to produce covering colored coatings. In this case, commonly used pigments, and optionally fillers, can be incorporated in the coating composition. While in accordance with the invention no additives are required as lubricating or separating agents, and preferably none are used, such substances, for example, silicic acid or talc, may be added during the coating process if this is considered desirable for other reasons.

White or colored pigments such as titanium dioxide, iron oxide pigments, or alumina lakes, are generally used in amounts of from 10 to 300 weight percent, based on the polymer. They can be mixed as such, or as a suspension in water, with the dispersion of the polymer. The lipophilic emulsifier may be added to the polymer dispersion or to the pigment suspension, or proportionately to both, prior to such mixing. To stabilize the pigment suspension, up to about 5 weight percent of the lipophilic emulsifier, based on the weight of the pigment, should be used. Its HLB value should preferably be in the upper portion of the claimed range from 3.5 to 7.

Other commonly used additives which may be used also in the coating compositions of the invention are soluble dyes from the group of permissible food colorants, polishing agents such as polyethylene glycols or waxes, defoaming agents, stabilizers, thickeners and the like.

Under normal ambient conditions, that is, in a closed container at temperatures not above $30°$ C., the coating composition composed in accordance with the invention and optionally incorporating additives of the type mentioned will keep for several weeks or months. It can therefore be put on the market formulated ready for use, shipped, and stored until it is used. Equipment for homogenization, stabilization and the like at the place where the coating composition is to be used can therefore be dispensed with.

Often it is advisable to dilute the coating composition before the spray coating operation to a concentration adapted to the spraying conditions. For use in a coating pan or in an air suspension chamber, polymer contents of from 5 to 25 weight percent are recommended.

Like conventional aqueous coating dispersions, the novel coating compositions are suitable for the coating of solid pharmaceutical dosage forms. They are preferably used to coat compact dosage forms that contain no major internal cavities, such as compressed tablets, dragées, pills, granules, pellets, particles, and crystals. Usual coating thicknesses range from 2 to 500 microns, and preferably from 10 to 200 microns. Coatings are obtained which are resistant to gastric juice and, depending on their composition, dissolve or at least swell and become diffusion-permeable in the neutral or weakly alkaline medium of intestinal juice. They can also be used to granulate powders, the granulations so produced being optionally compressed into tablets.

A better understanding of the present invention and of its many advantages will be had by referring to the following specific examples, given by way of illustration.

EXAMPLE 1

Spraying Suspension for Controlled-Release Coatings

A suspension prepared from 7.1 g of glycerine monostearate (HLB=3.5) and 516.7 g of water is heated with stirring to 65° C.-70° C., homogenized with an "Ultra-Turrax" high speed agitator, and cooled with stirring to 20° C.-30° C.

476.2 g of a 30 percent aqueous anionic dispersion of an emulsion polymer of 67 percent by weight of ethyl acrylate and 3 percent by weight of methyl methacrylate (trade name "Eudragit NE30D", Röhm GmbH, Darmstadt) are added to this suspension with stirring. The spraying suspension so obtained has a solids content of 15 percent by weight and a viscosity of about 500 mPa s. It is ready for use and storable.

0.75 kg of verapamil HCl pellets (0.3 to 1.25 mm; content of active ingredient 88 percent by weight) are sprayed with 393.75 g of the spraying suspension in an air suspension chamber at an inlet air temperature of 40° C. and a spraying rate of 10 g/min. Then they are dried for 2 hours at 40° C.

The coated pellets contain 7.5 percent by weight of coating material. In vitro they exhibit a delayed release of the active ingredient over a period of 8 hours.

EXAMPLE 2

Spraying Suspension for Controlled-Release Coatings

A mixture of 6.0 g of glycerine monostearate (HLB=3.5) and 570 g of water is heated with stirring to 65° C.-70° C. and, after the addition of 24 g of triethyl citrate, homogenized with an "Ultra-Turrax" high speed agitator and then cooled with stirring to 20° C.-30° C.

320 g of a 30 percent aqueous dispersion of a redispersed copolymer of 65 percent by weight of methyl methacrylate, 30 percent by weight of ethyl acrylate and 5 percent by weight of trimethylammoniumethyl methacrylate chloride are added to this suspension with stirring together with 80 g of a 30 percent aqueous dispersion of a redispersed copolymer of 60 percent by weight of methyl methacrylate, 30 percent by weight of ethyl acrylate and 10 percent by weight of trimethylammoniumethyl methacrylate chloride [trade names "Eudragit RS30D" and "Eudragit RL30D", Röhm GmbH, Darmstadt). A storable ready to use spraying suspension with a solids content of 15 percent by weight and a viscosity of about 500 mPa s is so obtained.

0.75 kg of theophylline granules (0.3 to 0.8 mm) are sprayed with 875 g of the spraying suspension in an air suspension chamber at an inlet air temperature of 40° C. and a spraying rate of 10 g/min. Then they are dried for 24 hours at 40° C. in a hot air oven.

The coated granules contain 14 percent by weight of coating material. In vitro they exhibit a release of the active ingredient delayed over a period of 8 hours.

EXAMPLE 3

Spraying Suspension for Enteric Coatings

A mixture of 3.7 g of glycerine monostearate and 465 g of water is heated with stirring to 65° C.-70° C. and, after the addition of 24.4 g of triethyl citrate (as a plasticizer), homogenized with a high speed agitator and then cooled with stirring to 20° C.-30° C.

406.5 g of a 30 percent aqueous dispersion of an emulsion polymer of 50 percent by weight of methacrylic acid and 50 percent by weight of ethyl acrylate (trade name "Eudragit L30D", Röhm GmbH, Darmstadt) are added to this suspension with stirring. A ready to use and storable spraying suspension with a solids content of 15 percent by weight and a viscosity of about 500 mPa s is so obtained.

2.8 kg of placebo tablets are sprayed with 1082.4 g of the spraying suspension in a rotating coating pan at an inlet air temperature of 50° C. and a spraying rate of 8-10 g/min. Then they are dried for 2 hours at 40° C. in a hot air oven.

The coated tablets contain 6 mg/cm$^2$ of coating material. They disintegrate in artificial intestinal fluid of pH 6.8 within 30 minutes.

EXAMPLE 4

Spraying Suspension for Taste-Masking Coatings

A mixture of 4 g of glycerine monostearate, 213.3 g of water, 16 g of triethyl citrate, and 266.7 g of a 30 percent aqueous dispersion of a dispersed copolymer of 60 percent by weight of methyl methacrylate, 30 percent by weight of ethyl acrylate, and 10 percent by weight of trimethylammoniumethyl methacrylate chloride (trade name "Eudragit RL30D", Röhm GmbH, Darmstadt) is heated with stirring to 65° C.-70° C., homogenized with a high speed agitator, and then cooled with stirring to 20° C.-30° C. The spraying suspension so obtained has a solids content of 20 percent by weight and a viscosity of about 500 mPa s. It is ready for use and storable.

137.5 g of this spraying suspension are then diluted with the same amount of water and sprayed onto 2.8 kg of verapamil HCl tablets in a rotating coating pan at an inlet air temperature of 50° C. and a spraying rate of 8-10 g/min. The tablets are then dried for 24 hours at 40° C. in a hot air oven.

The coated tablets contain 1 mg/cm$^2$ of coating material. They mask taste for about one minute and in vitro release more than 80 percent of the active ingredient within 15 minutes. (USP XXI, Meth. 2, 100 rpm, 0.1 normal hydrochloric acid.)

EXAMPLE 5

Surfactant-Containing Pigment Suspension

A mixture of 8 g of glycerine monostearate and 800 g of water is heated with stirring to 65° C.-70° C. and, after the addition of 32 g of triethyl citrate, homogenized with a high speed agitator. During homogenization, 53.3 g of a red pigment ("Sicopharm Red 30") and 106.7 g of titanium dioxide are added. The batch is then cooled with stirring to 20° C.-30° C.

The pigment suspension has a solids content of 20 percent by weight and sediments only slightly during prolonged storage. It can be mixed with aqueous coating dispersions to give spray coating suspensions. To this end, 245.5 g of the pigment suspension are diluted with 458.5 g of water and added with stirring to the dispersion used in Example 4 ("Eudragit RL30D").

5 kg of placebo tablets are then sprayed in a rotating coating pan with 884 g of this suspension at an inlet air temperature of 50° C. and a spraying rate of 11 g/min. The tablets are then dried for 24 hours at 40° C. in a hot air oven.

The coated tablets contain 1 mg/cm$^2$ of coating material. They disintegrate in vitro within about 2 minutes.

EXAMPLE 6

Agglutination-Reducing Surfactant Dispersion

A mixture of 10 g of glycerine monostearate and 950 g of water is heated with stirring to 65° C.–70° C., homogenized with an "Ultra-Turrax" high speed agitator, and then cooled with stirring to 20° C.–30° C. The surfactant dispersion is ready for use. It has a solids content of 1 percent by weight.

0.881 kg of the theophylline granules produced in Example 2 are sprayed with 88 g of the surfactant dispersion in an air suspension chamber at an inlet air temperature of 40° C. and a spraying rate of 10 g/min. Then they are dried for 24 hours at 40° C. in a hot air oven.

The granules, first coated with 14 percent by weight of coating material and then with 0.1 percent by weight of glycerine monostearate, no longer exhibit any tackiness and allow storage for an extended period.

EXAMPLE 7

Spraying Suspension for Rapidly Disintegrating Coatings

To prepare the spraying suspension, the same procedure is followed as in Example 4, but in place of glycerine monostearate the same amount of doubly ethoxylated stearyl alcohol (HLB=4.9) is used. 2.8 kg of placebo tablets are sprayed in a rotating coating pan with 137.5 g of the spraying suspension at an inlet air temperature of 50° C. and a spraying rate of 8–10 g/min. Then they are dried for 24 hours at 40° C. in a hot air oven. The tablets have disintegration times from 2 to 5 minutes.

EXAMPLES 8 AND 9

Spraying Suspension for Rapidly Disintegrating Coatings

The same procedure is followed as in Example 7, but in place of doubly ethoxylated stearyl alcohol the same amount of sorbitan monostearate (trade name "Span 60", HLB=4.7) or of glycerine monolaurate (HLB=5.6), respectively, is used. In both cases, tablets having disintegration times of from 2 to 5 minutes are obtained.

EXAMPLE 10

Comparison of (A) the Procedure of the Invention with (B) Operating Procedures Using Talc as a Parting Agent, and (C) Using No Parting Agent (A) A mixture of 2.4 g of glycerine monostearate, 19.1 g of triethyl citrate, and 982 g of water is homogenized with a high speed agitator after the addition of 0.1 g of 33 percent 20-fold ethoxylated sorbitan monooleate (["Tween 80", HLB=11.3). During homogenization, 47.8 g of a brown pigment ("Sicopharm Brown 70") and 47.8 g of titanium dioxide are added. This pigment suspension exhibits practically no sedimentation.

It is admixed with stirring with 318 g of the dispersion used in Example 4. 10 kg of placebo tablets are sprayed in a rotating coating pan with 1417 g of the suspension so obtained at an inlet air temperature of 50° C. and a spraying rate of 24 g/min. Then they are dried for 24 hours at 40° C. in a hot air oven. The coating weight is 1 mg/cm$^2$. The coating is smooth, glossy and uniform. The disintegration times of the coated tablets range from about 2 to 5 minutes. The tablets are unchanged after two months' storage.

(B) A suspension of 45 g of talc in 210 g of water is homogenized with an "Ultra-Turrax" high speed agitator after the addition of 9 g of polyethylene glycol (molecular weight=6000). During homogenization, 12 g of a yellow pigment, "E 104", and 24 g of titanium dioxide are added. This pigment suspension sediments completely within 30 minutes.

To prepare a sprayable pigment suspension, 300 g of the 30 percent suspension obtained is mixed with 6 g of triethyl citrate, diluted with 144 g of water, and mixed with 100 g of the dispersion used in Example 4. The suspension so obtained sediments after a short time.

550 g of the freshly homogenized suspension is sprayed in a rotating coating pan onto 3 kg of placebo tablets at an inlet air temperature of 50° C. and a spraying rate of 8 g/min. The coated tablets are then dried for 24 hours at 40° C. in a hot air oven. The coating weight is 1 mg/cm$^2$. The coating is smooth, glossy and uniform. The tablets have disintegration times of from 2 to 5 minutes.

(C) A mixture of 19.1 g of triethyl citrate and 982 g of water is homogenized with an "Ultra-Turrax" high speed agitator. During homogenization, 47.8 g of a brown pigment "Sicopharm Brown 70") and the same amount of titanium dioxide are added. This pigment suspension is added to 318 g of the dispersion used in Example 4.

10 kg of placebo tablets are then sprayed in a rotating coating pan with 1415 g of the suspension so obtained at an inlet air temperature of 50° C. and a spraying rate of 17 g/min. Despite the reduced spraying rate, there are unmistakable signs of agglutination during coating.

The coated tablets are dried for 24 hours at 40° C. in a hot air oven. The coating weight is 1 mg/cm$^2$. The coating is dull, rough, and uneven. The disintegration times of the coated tablets range from about 1 to 10 minutes.

EXAMPLE 11

Preparation of a Suspension for Spray Drying

A suspension of 5 g of glycerine monostearate and 362.8 g of water is heated to about 65° C. to 70° C. with stirring, homogenized with a high speed agitator ("Ultra Turrax"), and then cooled with stirring to 20° C.–30° C.

332.2 g of a polymer dispersion containing 30 percent solids is added to this suspension with stirring: The polymer consists of 60 percent by weight of butyl methacrylate, 10 percent of ethyl acrylate, and 30 percent of 3-dimethylamino-2,2-dimethylpropyl-1-methacrylate.

The polymer dispersion, which is ready for use, has a solids content of 15 percent and a viscosity of about 500 mPa s.

700 g of the suspension prepared in this manner are applied in a fluidized bed apparatus to 1.0 kg of norephedrine pellets (about 37 percent active ingredient) at an air inlet temperature of 40° C. using a spray velocity of 10 g/min.

After drying for 24 hours at room temperature, the coated pellets having a 10 percent coating show a complete release of the active ingredient after one hour in vitro in synthetic stomach juice at pH 1.3, and a delayed release of active ingredient over 4–5 hours in synthetic intestinal juice at pH 6.8.

EXAMPLE 12

Preparation of a Suspension for Spray Drying of a Delayed Release Coating

A suspension of 2.8 g of glycerine monostearate, 11.3 g of polyethylene glycol 6000, and 342.15 g of water is heated to about 65° C.–70° C. with stirring, homogenized with a high speed agitator ("Ultra Turrax"), and then cooled to 20° C.–30° C. while stirring.

112.5 g of a 50 percent dispersion of polybutyl methacrylate are added to this suspension.

468.7 g of the ready to use suspension made in this way are applied to 0.75 kg of verapamil HCl granulate (0.5–1.25 mm, content of active ingredient about 85 percent) at an air inlet temperature of 40° C. at a spray velocity of 10 g/min.

After drying for two hours in a circulating air cabinet at 40° C., the coated granulate having a coating of 7.5 percent shows a delayed release of the active ingredient over about 8 hours in vitro.

EXAMPLE 13

Preparation of Tablets Using 8 Percent Sorbitan Monooleate

A mixture of 10.37 g of sorbitan monooleate, 371.52 g of water, and 25.92 g of triethyl citrate is heated to 65° C. to 75° C. with stirring, homogenized with a rapid stirring apparatus ("Ultra Turrax"), and then cooled to 20° C. to 30° C. with stirring. This mixture is added to 432 g of a 30 percent by weight aqueous dispersion of an emulsion polymer of 50 percent by weight of methacrylic acid and 50 percent by weight of ethyl acrylate ("Eudragit L30D", Röhm GmbH, Darmstadt) A ready-to-use polymer dispersion having a solids content of 20 percent by weight and a viscosity of about 500 mPa s is obtained. The amount of polymer contained in the dispersion is 129.6 g. The amount of sorbitan monooleate, based on the weight of the polymer, is 8 percent.

The dispersion is applied to 3 kg of placebo tablets in a rotating coating kettle at an inlet air temperature of 50° C. and a spray rate of 9 g/min. During the spray application, the tablets have a very smooth feel. There is a slight deposit, usual for such coating procedures, in the coating kettle. From this it is clear that there is both a sufficient lubricating and parting or separating effect.

After drying for 24 hours in a circulating air over at 40° C., the coated tablets having a 6 mg/cm$^2$ coating thereon show the expected two hour resistance to synthetic stomach juice (British Pharmacopoeia 88).

EXAMPLE 14

Preparation of Tablets Using 10 Percent Sorbitan Monooleate

Example 13 is repeated with the difference that 12.96 g of sorbitan monooleate, which is 10 percent by weight of the polymer, is employed instead of 10.37 g. Again, a dispersion having a viscosity of about 500 mPa s is obtained.

Just as in Example 13, the dispersion is applied to 3 kg of placebo tablets in a rotating kettle at an air inlet temperature of 50° C. and a spray rate of 9 g/min. During the spray application the tablets feel very smooth, indicative of a sufficient lubricating effect. However, there is a heavy polymer deposit in the coating kettle, which is attributable to an insufficient parting or separating effect between the coating and the surface of the kettle.

After drying for 24 hours in a circulating air over at 40° C., the coated tablets, having a calculated polymer coating of 6 mg/cm$^2$, do not show the requisite two-hour resistance against synthetic stomach juice (BP 88). From this it is to be concluded that the coating on the tables was less uniform or thinner than that in Example 13.

What is claimed is:

1. A stable film forming aqueous coating composition for solid pharmaceutical dosage forms, comprising
   (a) an aqueous dispersion, prepared directly by aqueous emulsion polymerization, of a film forming polymer comprising at least one member selected from the group consisting of acrylic acid, methacrylic acid, alkyl esters of these acids, and aminoalkyl esters of these acids, and, added to said dispersion,
   (b) a water insoluble organic lipophilic emulsifier having a hydrophile-lipophile balance (HLB) value from 3.5 to 5, in an amount which is from 0.1 to 8 percent by weight of said polymer.

2. A coating composition as in claim 1 which further comprises a pigment in an amount from 10 to 300 percent by weight of said polymer.

3. A coating composition as in claim 1 wherein said emulsifier is sorbitan monooleate.

4. A coating composition as in claim 2 wherein said emulsifier is sorbitan monooleate.

5. A method for making a coating composition as in claim 2 which comprises mixing an aqueous dispersion of said film forming polymer with an aqueous mixture of said pigment and of said lipophilic emulsifier.

6. In a method for coating pharmaceutical dosage forms, the improvement wherein the composition of claim 1 is used in the absence of lubricants and parting agents.

7. A method as in claim 6 wherein said dosage forms are coated by a fluidized bed process.

8. A coating composition as in claim 1 wherein said emulsifier is glycerol monostearate.

9. A coating composition as in claim 2 wherein said emulsifier is glycerol monostearate.

* * * * *